United States Patent [19]
Stevens

[11] Patent Number: 5,741,278
[45] Date of Patent: *Apr. 21, 1998

[54] ENDOSCOPIC SUTURE PLACEMENT TOOL

[75] Inventor: Jon A. Stevens, Condado, Puerto Rico

[73] Assignee: Tahoe Surgical Instruments, San Juan, Puerto Rico

[*] Notice: The term of this patent shall not extend beyond the expiration date of Pat. No. 5,573,542.

[21] Appl. No.: 731,601

[22] Filed: Oct. 16, 1996

Related U.S. Application Data

[63] Continuation of Ser. No. 292,088, Aug. 17, 1994, Pat. No. 5,573,542.

[51] Int. Cl.$^6$ .................................................. A61B 17/04
[52] U.S. Cl. ........................... 606/144; 606/139; 606/148; 606/222; 606/223
[58] Field of Search ................................ 606/139, 144, 606/148, 222–223; 112/169, 80.03

[56] References Cited

U.S. PATENT DOCUMENTS

| | | | |
|---|---|---|---|
| 2,670,673 | 3/1954 | Gordon et al. | 99/257 |
| 4,103,690 | 8/1978 | Harris | 128/418 |
| 4,316,469 | 2/1982 | Kapitanov . | |
| 4,665,906 | 5/1987 | Jervis . | |
| 4,779,616 | 10/1988 | Johnson . | |
| 5,037,433 | 8/1991 | Wilk et al. | 606/144 |
| 5,067,957 | 11/1991 | Jervis | 606/108 |
| 5,190,546 | 3/1993 | Jervis | 606/78 |
| 5,219,358 | 6/1993 | Bendel et al. | 606/222 |
| 5,242,427 | 9/1993 | Bilweis | 604/264 |
| 5,250,054 | 10/1993 | Li | 606/144 |
| 5,250,055 | 10/1993 | Moore et al. | 606/148 |
| 5,281,234 | 1/1994 | Wilk et al. | 606/139 |
| 5,330,488 | 7/1994 | Goldrath | 606/148 |
| 5,364,410 | 11/1994 | Failla et al. | 606/148 |
| 5,387,227 | 2/1995 | Grice | 606/222 |
| 5,403,329 | 4/1995 | Hinchcliffe | 606/147 |
| 5,462,560 | 10/1995 | Stevens | 606/144 |
| 5,462,561 | 10/1995 | Voda | 606/148 |
| 5,486,183 | 1/1996 | Middleman et al. | 606/127 |
| 5,503,634 | 4/1996 | Christy | 606/144 |
| 5,573,542 | 11/1996 | Stevens | 606/144 |

FOREIGN PATENT DOCUMENTS

| | | | |
|---|---|---|---|
| 404226643 | 8/1992 | Japan | 606/222 |
| 969 254 | 10/1982 | U.S.S.R. . | |
| 0242110 | 11/1925 | United Kingdom | 112/80.03 |
| 0639845 | 7/1950 | United Kingdom | 112/80.03 |

OTHER PUBLICATIONS

R–Med, Inc. brochure, "Riza –Ribe Needle" undated, 5 pages.
Brochure –Ideas for Medicine Inc., Grice Suture Needle.
Brochure (in Japanese) CLINY "Percutaneous Gastropexy for Percutaneous Endoscopic Gastrostomy" The Birth of a Gastropexy Device.

Primary Examiner—Michael Buiz
Assistant Examiner—Tina T. D. Pham
Attorney, Agent, or Firm—Limbach & Limbach L.L.P.

[57] ABSTRACT

A surgical tool for endoscopic suture placement which permits a surgeon to place controlled and precise internal ligatures. The tool utilizes a drive rod including an articulating or deflecting portion. When forced to an extended position, the deflecting or articulating portion forms a hook or J-shaped needle, the tip of which can be used to accurately position the suture.

6 Claims, 2 Drawing Sheets

ENDOSCOPIC SUTURE PLACEMENT TOOL

This is a continuation of application Ser. no. 08/292,088, filed Aug. 17, 1994,. now U.S. Pat. No. 5,573,542.

FIELD OF THE INVENTION

This invention relates to medical devices used to place controlled and precise internal ligatures. The device is particularly useful for endoscopic suture placement.

BACKGROUND OF THE INVENTION

During endoscopic surgery, precise placement of ligatures is required. Commonly, during endoscopic and other surgeries, sutures are placed using any number of devices. However, such devices require extreme dexterity and care on the part of the surgeon in order to reach the necessary position without dropping the suture. Thus, it would be desireable to identify a device which would permit a surgeon to precisely place internal ligatures in a controlled manner.

SUMMARY OF THE INVENTION

Accordingly, the present invention is a ligature device including an outer sheath having a distal end, a drive rod slidably mounted to said outer sheath for movement between a retracted position and an extended position, the drive rod including a deflecting portion having means for holding a ligature, the deflecting portion being at least partially confined within the outer sheath and having a first shape when the drive rod is in the retracted position, the deflecting portion extending from the distal end of the outer sheath and having a second shape when the drive rod is in the extended position, the first and second shapes being different, and a movable actuator attached to the drive rod for moving the drive rod between the retracted and extended positions.

In one form of the invention, the ligature holding means includes a passage extending inwardly from an outer surface of the deflecting portion, the transverse passage terminating at an eyelet.

In another form of the invention, the deflecting portion is made of a shape memory alloy.

In yet another form of the invention the device includes means for biasing the drive rod toward the retracted position. Such biasing means can be a coil spring.

In a preferred form of the invention the first shape of the deflecting portion is substantially linear and the second shape is curved to form a hook or J-shape.

In order to promote stability, the outer sheath may include a hollow interior having a square cross-sectional shape.

In another form of the invention, the deflecting portion is completely housed within the outer sheath when the drive rod is in the retracted position.

BRIEF DESCRIPTION OF THE DRAWINGS

The invention will be better understood by reference to the appended drawings of which.

DETAILED DESCRIPTION OF THE INVENTION

Figure 1:
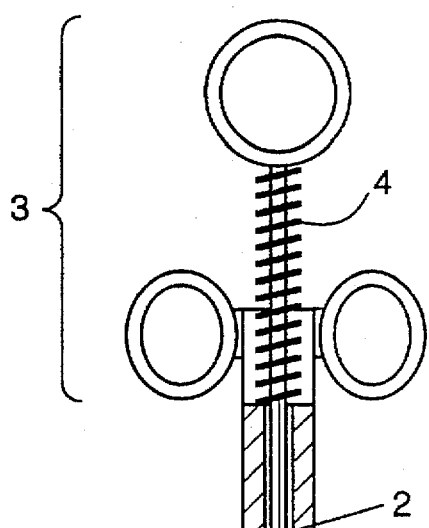
FIG. 1 is cross-sectional side view of a preferred embodiment of the invention in its relaxed or rod retracted position.
Figure 2:
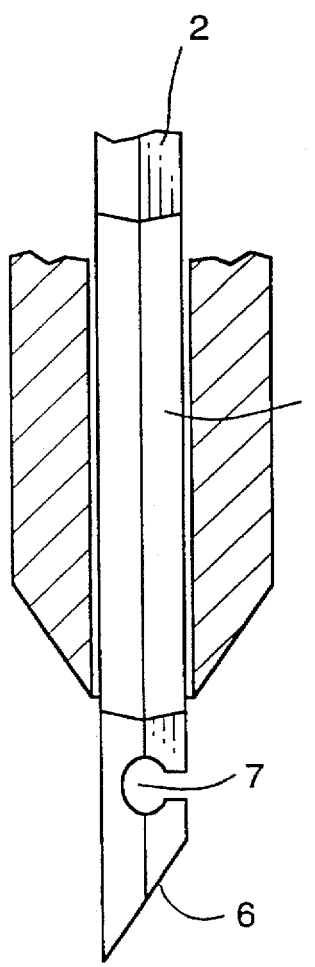
FIG. 2 is an enlarged cross-sectional side view of the distal end of the device showing the position of the suture tip when the device is in a rod retracted position.
Figure 3:
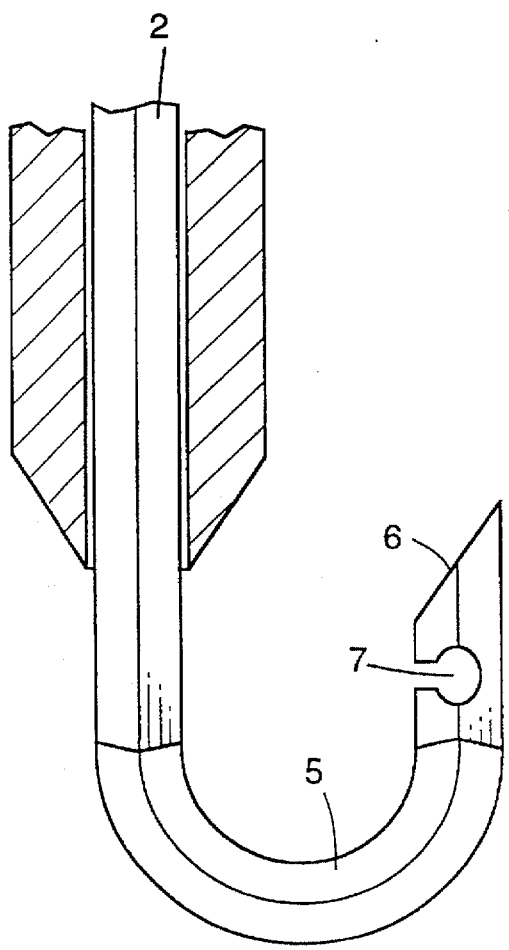
FIG. 3 is an enlarged cross-sectional side view of the distal end of the device showing the position of the suture tip when the device is in a rod extended position.
Figure 4A:
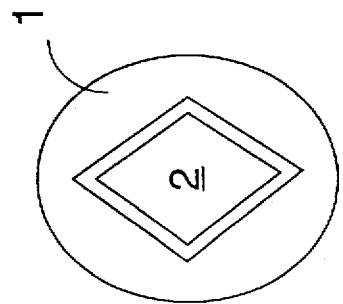
Figure 4B:
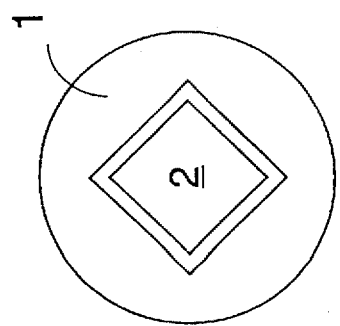

The apparatus of the invention is shown in detail in FIGS. 1–3.

Referring to FIG. 1, the endoscopic suture placement device of the invention is shown in a side, cross-sectional view. As can be seen, the device is made up of an outer sheath or housing 1, which is an extended, tubular-shaped sheath on or in which the other components of the device are mounted. In the preferred embodiment shown, the length of the outer housing will be approximately 450 mm, and will include a passage into which drive rod 2 is positioned. Housing 1 can be made of any structurally adequate material which can be medically approved such as plastics, metals, composites, ceramics, and the like, as are well known in the art. For structural purposes, and to ensure that drive rod 2 does not twist when in use, it is preferred that the cross-section of the passage in which the drive rod 2 is positioned is square or diamond shaped. Likewise, the cross-section of drive rod 2 will match that of the passage through the housing. Generally, the length of a side of the diamond-shaped cross-section of drive rod 2 will be from about 1–2 mm. The passage will, of course, be slightly larger to accommodate movement of the drive rod.

Movement of drive rod 2 from the rod retracted position shown in FIGS. 1 and 2 is accomplished using hand actuator 3, which, as seen in FIG. 1, consists of three finger/thumb rings, though many different handle/actuator configurations are possible. In use, the surgeon will grasp the device using finger/thumb rings in the same manner as holding a syringe. A spring 4 is mounted surrounding a proximal portion of drive rod 2 and supported within housing 1 to bias the rod to a retracted position.

The fourth key component of the invention is a deflecting portion 5 of drive rod 2 positioned at the distal end of drive rod 2 and between drive rod 2 and a suture tip 6.

Deflecting portion 5 is preferably formed from a filament of shape memory alloy (SMA), such as Ni/Ti alloy. SMA of the type useful in the present invention is available from Shape Memory Applications, Inc. of Sunnyvale, Calif., under the name NiTi Super Elastic Wire Cr-Dp. It should be recognized, however, that many other materials can be used, so long as they meet the performance requirements for the deflecting portion, i.e. that they will form an "arc" when extended from the housing by motion of the actuator, so that the surgeon gains the advantage of being able to place the suture underneath the tissue by pulling the device back toward him or her.

Labels in FIG. 2 indicate the same components as in FIG. 1. Also, as in all views, components are shown as spaced from one another for clarity and are not to scale. As can be seen, suture eyelet 7 is shown in FIG. 2.

FIG. 3 shows an enlarged cross-sectional view of the distal portion of the device when drive rod 2 is in its extended position. In this position, deflecting portion 5 returns to its "memorized" curved or hooked configuration, thereby forming a J-shaped hook at the distal end of the device.

In use, the surgeon will first position a suture in suture tip 6, secured in suture eyelet 7, then position the tip at the desired position in the patient's body, force the tip to the extended J-shaped configuration, which forces the suture tip and suture through the desired tissue. Suture placed laparoscopically requires the ability to penetrate multiple tissue planes with precise control. The device of the invention provides this action through the use of the described embodiments.

The invention can be used for many different kinds of procedures including, but not limited to, laparoscopic hysterectomy, laparoscopic Birtch and laparoscopic Nissan procedures.

Although only the most preferred embodiment of the invention has been shown and described. Many modifications and rearrangements of the components of the invention, which nevertheless include the key features thereof, will be apparent to those skilled in the art. Thus, such modifications are considered to be within the scope of the appended claims.

What is claimed:

1. A surgical tool including:
   a tubular, elongated housing having a proximal end, a distal end, and a passage defining a rod axis therethrough;
   a tissue piercing tip including means for supporting a ligature;
   a suture tip drive rod positioned within said passage, and moveable along the length thereof from a drive rod retracted position, wherein the tissue piercing tip is coaxial with the tip drive rod, to a drive rod extended position; and
   deflecting means comprising a shape memory portion secured on a first end to a distal portion of said drive rod and on a second end to said tissue piercing tip for deflecting said tissue piercing tip from said axis when said rod is in said extended position.

2. A surgical tool including:
   a tubular housing having a proximal end, a distal end, and a passage defining a rod axis therethrough;
   a tissue piercing tip portion including a means for supporting a ligature;
   a tip drive rod positioned within said passage, and moveable along a length thereof from a drive rod retracted position, wherein the tissue piercing tip is coaxial with the tip drive rod, to a drive rod extended position; and
   deflecting means comprising a shape memory portion secured on a first end to a distal portion of said drive rod and on a second end to said tissue piercing tip for causing said portion, in combination with said tip, to form a J-shaped hook when said drive rod is moved to said extended position.

3. The surgical tool of claim 2 wherein said means for supporting a ligature comprises an eyelet shaped to carry a ligature.

4. A surgical tool including:
   a tubular housing having a proximal end, a distal end, and a passage defining a rod axis therethrough;
   a tip portion having a tissue piercing end and a connecting end, and including an opening capable of carrying a ligature;
   a tip drive rod positioned within said passage, and moveable along a length thereof from a drive rod retracted position, wherein the tissue piercing end is coaxial with the tip drive rod, to a drive rod extended position; and
   a deflecting portion secured on a first end to said drive rod and on a second end to said connecting end of said tip for causing said portion to form an arc of substantially semicircular shape and to cause said tissue piercing end of said tip portion in a direction toward said proximal end of said housing when said drive rod is moved to said extended position.

5. A surgical tool including:
   a rigid tubular housing having a proximal end, a distal end, and a passage defining a rod axis therethrough, wherein said tubular housing is fixed relative to said rod axis;
   a tissue piercing tip including means for supporting a ligature;
   a suture tip drive rod positioned within said passage, and moveable along the length thereof from a drive rod retracted position, wherein the tissue piercing tip is coaxial with the tip drive rod, to a drive rod extended position; and
   deflecting means comprising a shape memory portion secured on a first end to a distal portion of said drive rod and on a second end to said tissue piercing tip for deflecting said tissue piercing tip from said axis when said rod is in said extended position.

6. A surgical tool including:
   a tubular housing having a proximal end, a distal end, and a passage defining a rod axis therethrough;
   a tissue piercing tip portion including a means for supporting a ligature;
   a tip drive rod positioned within said passage, and moveable along a length thereof from a drive rod retracted position to a drive rod extended position, wherein said tissue piercing tip is substantially contained within said tubular housing when said tip drive rod is in said retracted position; and
   deflecting means comprising a shape memory portion secured on a first end to a distal portion of said drive rod and on a second end to said tissue piercing tip for causing said portion, in combination with said tip, to form a J-shaped hook when said drive rod is moved to said extended position.

* * * * *